United States Patent
Grover

(10) Patent No.: US 12,053,232 B2
(45) Date of Patent: Aug. 6, 2024

(54) INTERNAL STRUCTURE OF A ROBOTIC SURGICAL INSTRUMENT

(71) Applicant: CMR SURGICAL LIMITED, Cambridge (GB)

(72) Inventor: Simon Roderick Grover, Cambridge (GB)

(73) Assignee: CMR Surgical Limited, Cambridge (GB)

(*) Notice: Subject to any disclaimer, the term of this patent is extended or adjusted under 35 U.S.C. 154(b) by 604 days.

(21) Appl. No.: 17/295,510

(22) PCT Filed: Nov. 29, 2019

(86) PCT No.: PCT/GB2019/053379
§ 371 (c)(1),
(2) Date: May 20, 2021

(87) PCT Pub. No.: WO2020/109812
PCT Pub. Date: Jun. 4, 2020

(65) Prior Publication Data
US 2022/0000540 A1    Jan. 6, 2022

(30) Foreign Application Priority Data
Nov. 29, 2018   (GB) ................................ 1819475

(51) Int. Cl.
*A61B 18/12*   (2006.01)
*A61B 18/14*   (2006.01)
(Continued)

(52) U.S. Cl.
CPC ...... *A61B 18/1445* (2013.01); *A61B 18/1482* (2013.01); *A61B 34/30* (2016.02);
(Continued)

(58) Field of Classification Search
CPC . A61B 17/29; A61B 18/1445; A61B 18/1482; A61B 34/30; A61B 34/71
See application file for complete search history.

(56) References Cited

U.S. PATENT DOCUMENTS 9,402,679 B2   8/2016   Ginnebaugh et al.
10,384,356 B2  8/2019   Lohmeier et al.
(Continued)

FOREIGN PATENT DOCUMENTS

CN   101801284 B   10/2012
CN   104411266 B   1/2019
(Continued)

OTHER PUBLICATIONS

International Search Report and Written Opinion issued Mar. 3, 2020, for related International Patent Application No. PCT/GB2019/053379.
(Continued)

*Primary Examiner* — Daniel W Fowler
(74) *Attorney, Agent, or Firm* — Renner, Otto, Boisselle & Sklar, LLP

(57) ABSTRACT

A robotic surgical instrument comprising a shaft, an end effector, and an articulation connecting the end effector to a distal end of the shaft. The articulation comprises joints permitting the end effector to adopt a range of orientations relative to a longitudinal axis of the shaft. Pairs of driving elements drive the joints, the driving elements extending through the shaft to the joints. An additional element extends through the shaft to the end effector via the articulation. A resilient barrier inside the shaft extends over a cross-sectional area of the shaft, the pairs of driving elements and the additional element passing through the resilient barrier, the resilient barrier being in resilient contact with the additional element so as to provide a resilient force opposing movement of the additional element; wherein each driving ele-
(Continued)

ment of the pairs of driving elements passes through a hole in the resilient barrier without contacting the resilient barrier.

18 Claims, 7 Drawing Sheets

(51) Int. Cl.
  *A61B 34/30* (2016.01)
  *A61B 18/00* (2006.01)
(52) U.S. Cl.
  CPC ............... *A61B 2018/00208* (2013.01); *A61B 2018/00595* (2013.01)

(56) References Cited

U.S. PATENT DOCUMENTS

| | | | |
|---|---|---|---|
| 11,317,909 | B2 | 5/2022 | Whitman et al. |
| 2005/0240218 | A1* | 10/2005 | Freed ..................... A61B 10/06 606/205 |
| 2009/0216248 | A1* | 8/2009 | Uenohara ............... A61B 34/70 606/130 |
| 2009/0326530 | A1* | 12/2009 | Orban, III ............... A61B 34/71 606/51 |
| 2010/0016852 | A1* | 1/2010 | Manzo ............... A61B 18/1445 606/41 |
| 2016/0193001 | A1 | 7/2016 | Lee et al. |
| 2016/0193012 | A1* | 7/2016 | Anderson ............... A61B 90/70 606/130 |
| 2017/0165016 | A1* | 6/2017 | Chaplin ................. A61B 34/37 |
| 2019/0099231 | A1* | 4/2019 | Bruehwiler .............. B25J 17/02 |
| 2019/0298466 | A1* | 10/2019 | Klein ..................... A61B 34/70 |

FOREIGN PATENT DOCUMENTS

| | | |
|---|---|---|
| EP | 2095778 A1 | 9/2009 |
| GB | 2563631 A | 12/2018 |
| JP | 2009226194 A | 10/2009 |
| JP | 2011521723 A1 | 7/2011 |
| WO | 2011024888 A1 | 3/2011 |
| WO | 2012112705 A1 | 8/2012 |

OTHER PUBLICATIONS

Search Report issued May 13, 2019, for priority Application No. GB1819475.3.
First Office Action issued May 31, 2022, for corresponding Japanese Patent Application No. 2021-527239.
First Office Action issued Jan. 2, 2024, for Chinese Application No. 201980078155.8.

\* cited by examiner

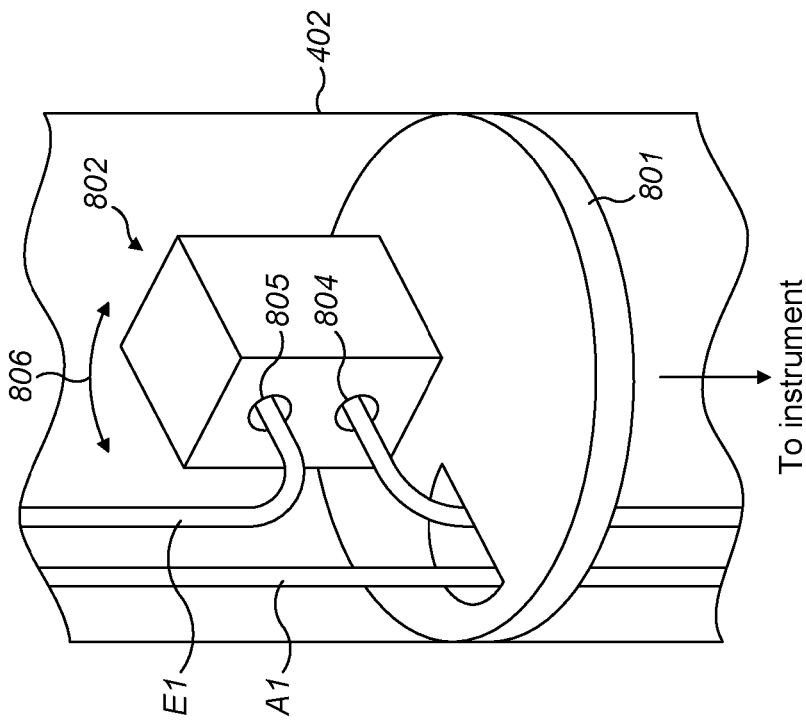
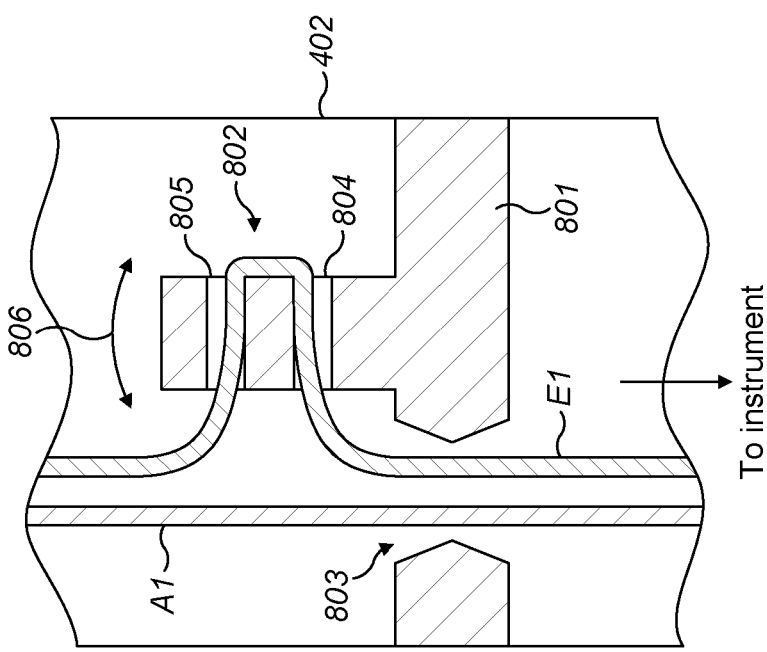

INTERNAL STRUCTURE OF A ROBOTIC SURGICAL INSTRUMENT

BACKGROUND

This disclosure relates to surgical instruments for use in robotic laparoscopic surgery.

FIG. 1 illustrates multiple robots 101, 102, 103 operating in a common workspace. In this example, the robots are surgical robots being used to perform an operation on a person 104. Each robot comprises a base connected to a surgical instrument via a flexible arm. The surgical instrument penetrates the body of the patient 104 at a port so as to access the surgical site. At its distal end, the instrument comprises an end effector for engaging in a surgical procedure.

A variety of end effectors are known, each adapted to perform a particular surgical function. FIG. 2 illustrates a surgical instrument 200 having a pair of serrated jaws 204 as the end effector. The surgical instrument comprises an interface 201 by means of which the surgical instrument connects to the robot arm. A shaft 202 extends between the interface 201 and an articulation 203. Articulation 203 terminates in the end effector 204. The articulation 203 permits the end effector 204 to move relative to the shaft 202. It is desirable for at least two degrees of freedom to be provided to the motion of the end effector 204 by means of the articulation.

SUMMARY OF THE INVENTION

According to an aspect of the invention, there is provided a robotic surgical instrument comprising: a shaft; an end effector; an articulation connecting the end effector to a distal end of the shaft, the articulation comprising joints permitting the end effector to adopt a range of orientations relative to a longitudinal axis of the shaft; pairs of driving elements configured to drive the joints, the driving elements extending through the shaft to the joints; an additional element extending through the shaft to the end effector via the articulation; and a resilient barrier inside the shaft extending over a cross-sectional area of the shaft, the pairs of driving elements and the additional element passing through the resilient barrier, the resilient barrier in resilient contact with the additional element so as to provide a resilient force opposing movement of the additional element; wherein each driving element of the pairs of driving elements passes through a hole in the resilient barrier without contacting the resilient barrier.

The resilient barrier may be configured to inhibit passage of fluid through the shaft from one side of the resilient barrier to the other. The resilient barrier may be configured to inhibit passage of insufflation gas through the shaft from one side of the resilient barrier to the other.

The cross-sectional area may be transverse to the longitudinal axis of the shaft.

An outer edge of the resilient barrier may be in sealed contact with the interior wall of the shaft around the outer edge of the cross-sectional area.

The additional element may pass through an additional hole in the resilient barrier, the diameter of the additional hole in the resilient barrier being less than or the same as the diameter of the additional element where it passes through the additional hole in the resilient barrier.

The robotic surgical instrument may be an electrosurgical instrument having an electrosurgical end effector, the additional element being an electrosurgical element configured to provide power to the electrosurgical end effector.

The resilient barrier may be located at the distal end of the shaft.

The additional element may be secured to one of the driving elements in a first portion of the shaft, the resilient barrier being located between the first portion of the shaft and the articulation.

The additional element may be secured to a spoke of the driving element in the first portion of the shaft.

The robotic surgical instrument may further comprise an instrument interface connected to a proximal end of the shaft, the instrument interface having an open structure through which fluid can move.

The additional element may be configured to wrap around at least one revolution of a joint of the articulation when the instrument is in a straight configuration in which the end effector is aligned with the shaft.

The resilient barrier may be fabricated from silicone.

The portion of the additional element which passes through the resilient barrier may be flexible.

The additional element may be a cable.

The robotic surgical instrument may further comprise a further additional element extending through the resilient barrier in the shaft to the end effector via the articulation, the further additional element in resilient contact with the resilient barrier.

The end effector may comprise first and second end effector elements, the additional element being connected to the first end effector element, the further additional element being connected to the second end effector element.

The additional element may be configured to provide power to the first end effector element, and the further additional element may be configured to provide power to the second end effector element.

BRIEF DESCRIPTION OF THE FIGURES

The present invention will now be described by way of example with reference to the accompanying drawings. In the drawings:

FIG. 8(a) illustrates a side view of an embodiment of a surgical instrument with a resilient barrier; and FIG. 8(b) illustrates an isometric view of an embodiment of a surgical instrument with a resilient barrier.

DETAILED DESCRIPTION

Figure 3:
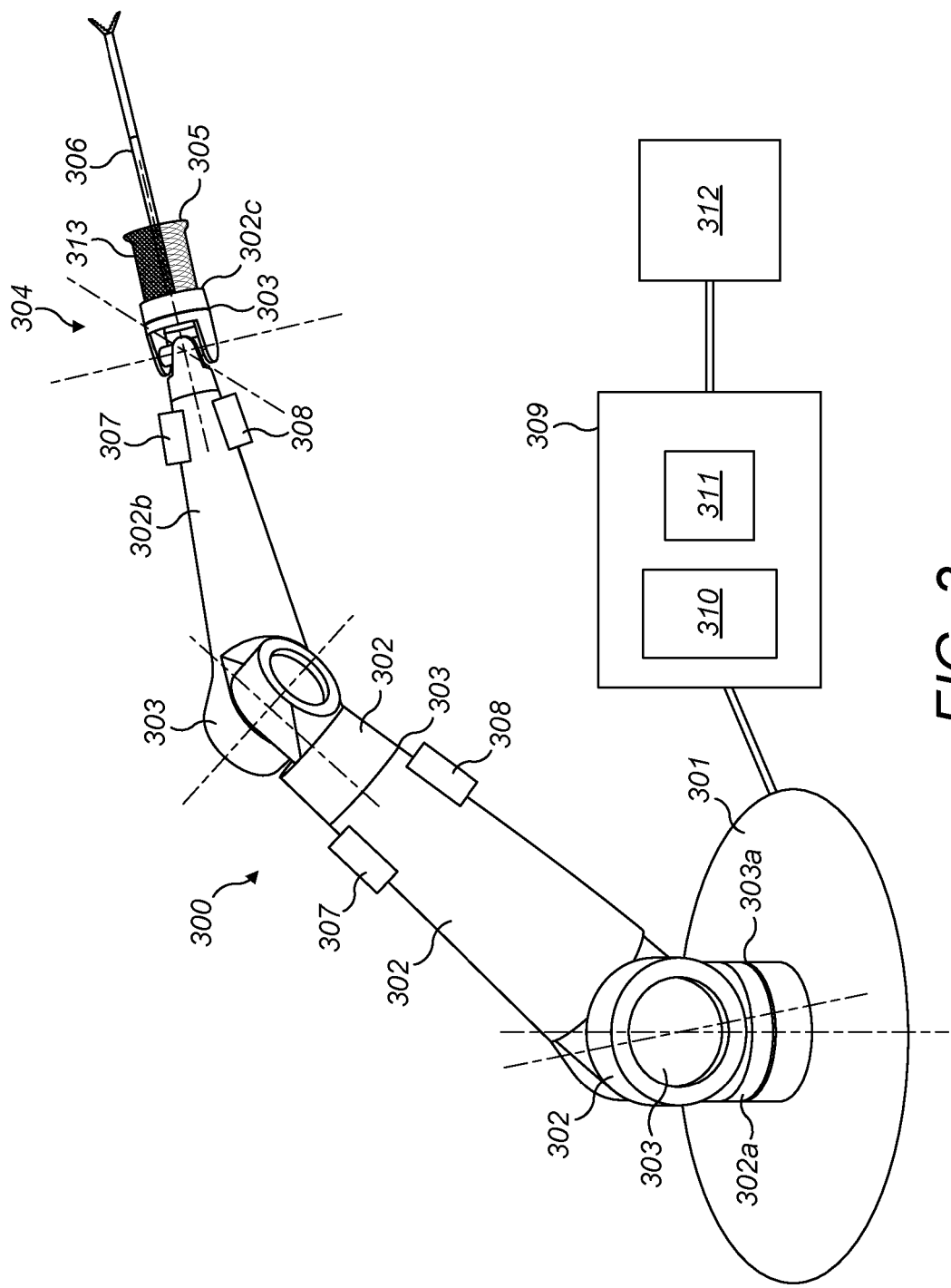
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by joint 303a. It and the other limbs are coupled in series by further ones of the joints 303. Wrist 304 couples one limb (302b) to the most distal limb (302c) of the arm. The most distal limb 302c has an arm interface 305 for interfacing a surgical instrument 306. Each joint 303 of the arm has one or more motors 307 which can be operated to cause rotational motion at the respective joint, and one or more position and/or torque sensors 308 which provide information regarding the current configuration and/or load at that joint. For clarity, only some of the motors and sensors are shown in FIG. 3. The arm may be generally as described in the applicant's co-pending patent application PCT/GB2014/053523.

Figure 1:
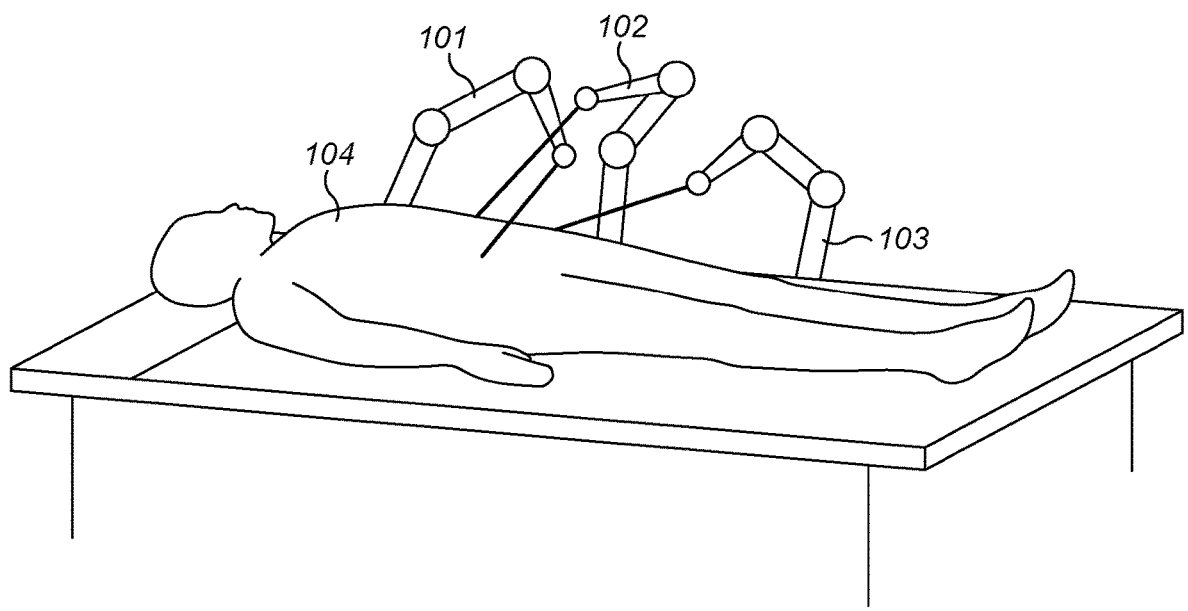
FIG. 1 illustrates a person being operated on by a robotic system comprising three surgical robots.
Figure 2:
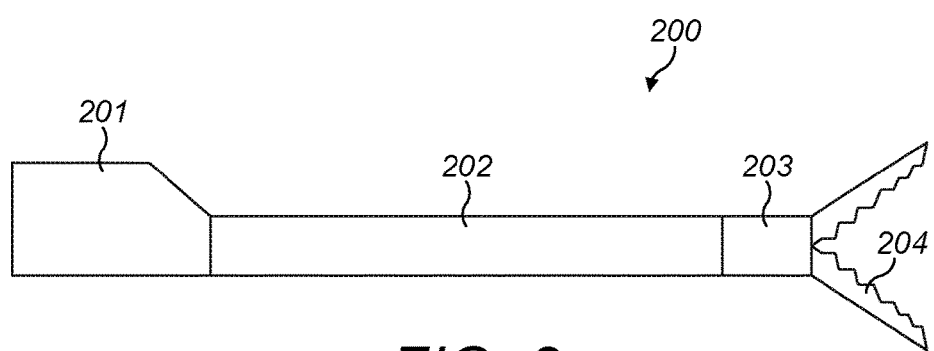
FIG. 2 illustrates a known surgical instrument.

The arm terminates in an arm interface 305 for interfacing with an instrument interface 313 of the instrument 306. Suitably, the instrument 306 takes the form described with respect to FIG. 2. The instrument has a diameter less than 8 mm. Suitably, the instrument has a diameter less than 6 mm. The instrument diameter may be between 5 mm and 6 mm. The instrument diameter may be the diameter of the shaft. The instrument diameter may be the diameter of the profile of the articulation. Suitably, the diameter of the profile of the articulation matches or is narrower than the diameter of the shaft. The arm interface 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation.

Controllers for the motors, torque sensors and encoders are distributed with the robot arm. The controllers are connected via a communication bus to control unit 309. A control unit 309 comprises a processor 310 and a memory 311. Memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in memory 311 is configured to respond to those inputs and cause the joints of the arm and instrument to move accordingly, in compliance with a pre-determined control strategy.

Figure 4:
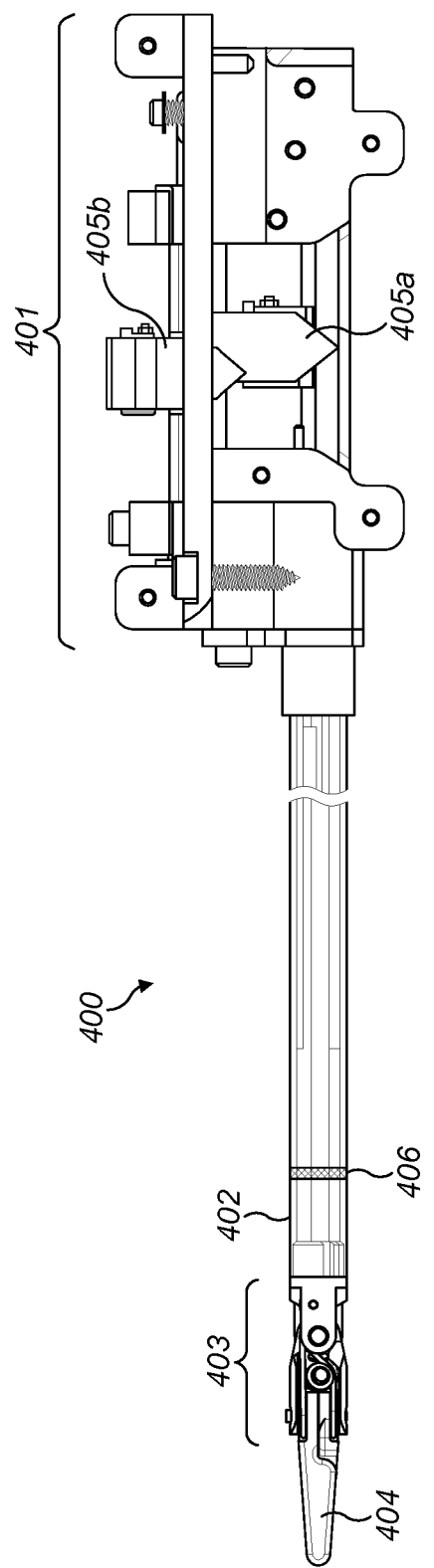
FIG. 4 illustrates a surgical instrument.

FIG. 4 illustrates a surgical instrument 400. The middle portion of the shaft is omitted for ease of illustration. The end effector 404 is connected to the shaft 402 by articulation 403.

Figure 5:
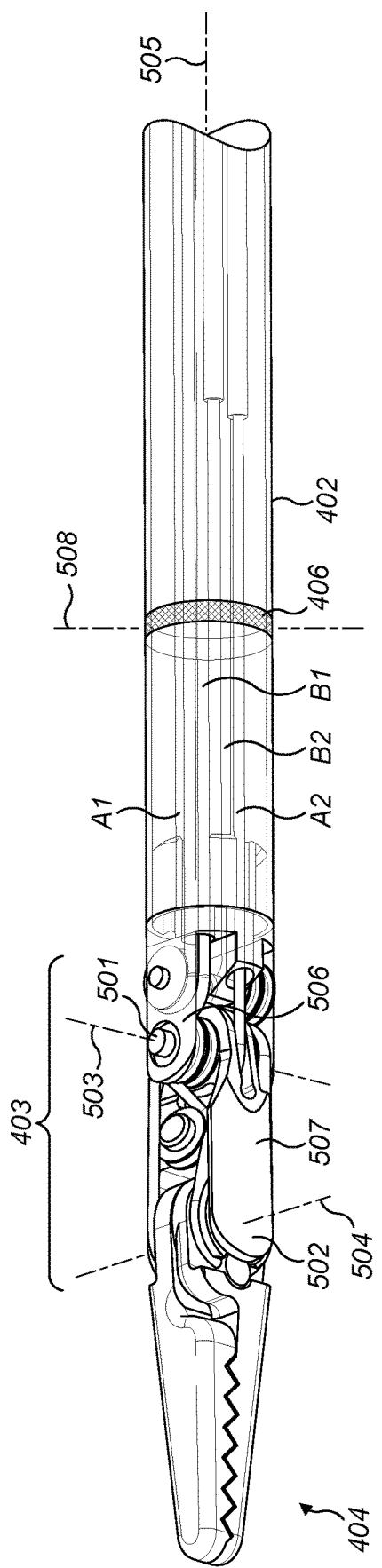
FIG. 5 illustrates a distal end of a surgical instrument.

FIG. 5 illustrates the distal portion of the surgical instrument 400 in more detail. The articulation 403 comprises joints which permit the end effector 404 to move relative to the shaft 402. A first joint 501 permits the end effector 404 to rotate about a first axis 503. The first axis 503 is transverse to the longitudinal axis of the shaft 505. A second joint 502 permits the end effector 404 to rotate about a second axis 504. The second axis 504 is transverse to the first axis 503. Thus, articulation of the first and second joints enables the end effector to take a range of attitudes relative to the shaft.

The articulation 403 comprises a first body part 506 and a second body part 507. The first body part connects the shaft 402 to the second body part 507. The first body part 506 is fast with the shaft 402. The first body part is connected to the second body part by the first joint 501. The second body part 507 connects the first body part 506 to the end effector 404. The second body part 507 is connected to the first body part by the first joint 501, and is connected to the end effector 404 by the second joint 502. Thus, the first joint 501 permits the second body part 507 to rotate relative to the shaft 402 about the first axis 503; and the second joint 502 permits the end effector 404 to rotate relative to the second body part 507 about the second axis 504.

The joints of the articulation are driven by driving elements. The driving elements are elongate elements which extend from the joints in the articulation through the shaft to the instrument interface. The driving elements are secured to the interface elements of the instrument interface. Thus, the robot arm transfers drive to the end effector as follows: movement of a drive assembly interface element moves an instrument interface element which moves a driving element which moves a joint of the articulation which moves the end effector. Suitably, each driving element can be flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements are not flexible along their main extents. The driving elements resist compression and tension forces applied along their length. In other words, the driving elements resist compression and tension forces acting in the direction of their longitudinal axes. The driving elements have a high modulus. The driving elements remain taut in operation. They are not permitted to become slack.

Thus, the driving elements are able to transfer drive from the instrument interface to the joints. The driving elements may be cables.

In the example shown in FIG. 5, the first joint 501 is driven by a first pair of driving elements A1, A2, and the second joint 502 is driven by a second pair of driving elements B1, B2. Suitably, each joint is driven by its own pair of driving elements. In other words, each joint is driven by a dedicated pair of driving elements. Suitably, the joints are independently driven. A pair of driving elements may be constructed as a single piece. This single piece may be secured to the joint at one point, thereby ensuring that when the pair of driving elements is driven, the drive is transferred to motion of the joint about its axis. Alternatively, a pair of driving elements may be constructed as two pieces. In this case, each separate piece is secured to the joint.

Each pair of driving elements is connected to an instrument interface element 405a, 405b of the instrument interface 401 at the proximal end of the shaft. The instrument interface 401 may have a structure which is open to the passage of fluids. In such a structure, gas/liquid in the shaft 402 passes through and out of the instrument interface 401 uninhibited.

For abdominal laparoscopic surgery, the abdominal cavity is typically inflated with insufflation gas (such as $CO_2$) so as to enable the surgeon better visibility of and access to the surgical site. However, when using an instrument of the type described with reference to FIGS. 4 and 5, the insufflation gas may escape from the surgical site through the interior of the shaft of the surgical instrument and out through the open structure of the instrument interface of the surgical instrument. This problem does not arise in instruments having an instrument interface structure which is substantially closed to the passage of fluids.

The instrument shaft of FIGS. 4 and 5 may comprise a resilient barrier 406 which extends across a cross-sectional area of the shaft. The cross-sectional area may be transverse to the longitudinal axis 505 of the shaft. For example, the cross-sectional area may be in a plane comprising an axis 508 perpendicular to the longitudinal axis 505 of the shaft. Alternatively, the cross-sectional area may be in a plane at an angle to both axis 508 and longitudinal axis 505 of the shaft. Suitably, the outer edge of the resilient barrier 406 is in sealed contact with the interior wall of the shaft at all points around the outer edge of the cross-sectional area. Suitably, the resilient barrier 406 is fabricated from a material which inhibits the passage of fluid through it. Thus, the resilient barrier 406 acts as a stopper or a bung, inhibiting the passage of fluid (such as the insufflation gas) through the shaft from the side of the resilient barrier facing the articulation to the opposing side of the resilient barrier facing the interior of the shaft. The resilient barrier 406 is internal to the shaft 402. The resilient barrier 406 may be located anywhere along the shaft. Preferably, the resilient barrier 406 is located in the distal end of the shaft proximal to the end effector 404. The closer the resilient barrier 406 to the distal end of the shaft, the less insufflation gas that can leak from the surgical site into the instrument before being inhibited by the resilient barrier.

Figure 6B:
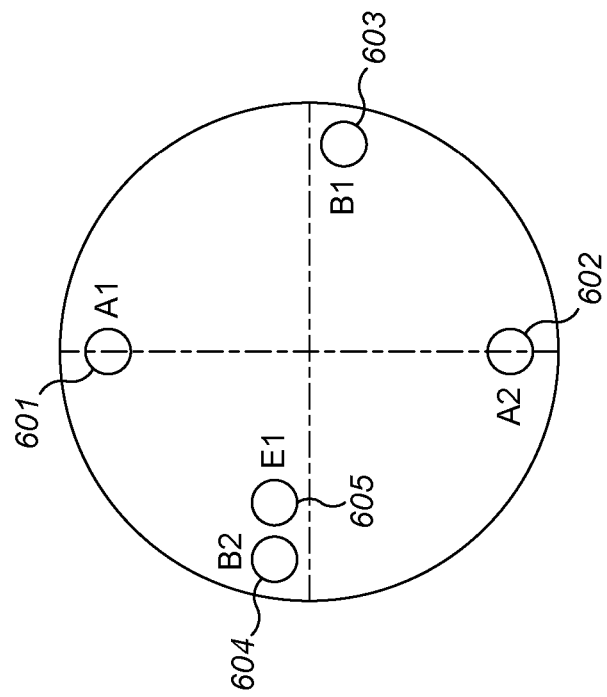
FIGS. 6a and 6b illustrate plan views of resilient barriers.
Figure 6A:
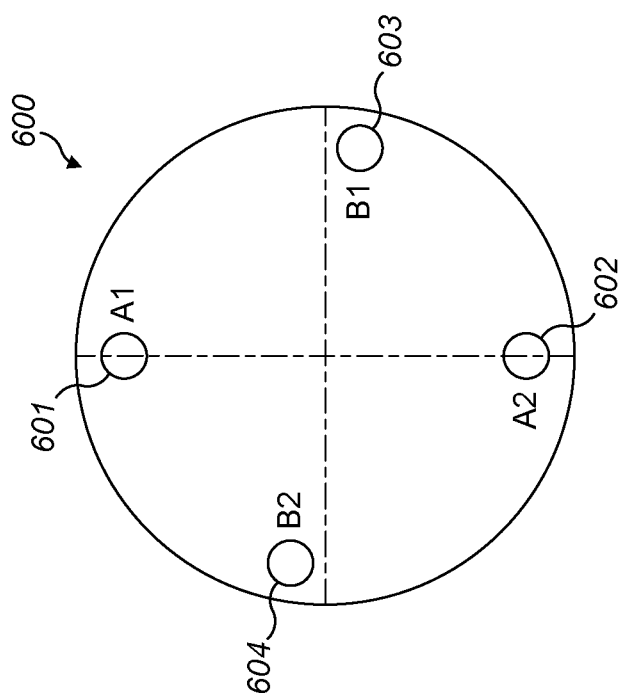

FIG. 6*a* illustrates an exemplary plan view of a resilient barrier 406. The pairs of driving elements A1, A2 and B1, B2 driving the joints of the articulation 403 pass through the resilient barrier 406. Suitably, each driving element passes through a hole in the resilient barrier 406. In the example of FIG. 6*a*, A1 passes through hole 601, A2 passes through hole 602, B1 passes through hole 603 and B2 passes through hole 604. Each driving element may pass through the resilient barrier 406 without contacting the resilient barrier 406. This may be achieved, for example, by the diameter of each hole being greater than the diameter of the driving element which passes through it. In this case, the resilient barrier 406 does not constrain the driving elements at all. In other words, there is no interaction between the resilient barrier 406 and the driving elements. As a result of the holes not contacting the driving elements, the resilient barrier does not wholly seal the interior of the shaft from fluid contacting the resilient barrier from the surgical site. However, the resilient barrier provides an effective block to fluid so as to substantially block the passage of insufflation gas and hence reduce the leakage rates experienced with instruments of the type shown in FIGS. 4 and 5.

Alternatively, each driving element may pass through the resilient barrier 406 contacting the resilient barrier 406. This may be achieved, for example, by the diameter of each hole being less than the diameter of the driving element which passes through it. There is very little frictional contact between the driving element and the resilient barrier. Specifically, the frictional force acting on the driving element as a result of its contact with the resilient barrier is less than a threshold frictional value. This threshold frictional value may be a value 1.5N. For example, the threshold frictional value may be 1.5N. The threshold frictional value may be a value 0.5N. For example, the threshold frictional value may be 0.5N. The threshold frictional value may be a value 0.1N. For example, the threshold frictional value may be 0.1N. This may be achieved, for example, by lubricating the contact area of the resilient barrier 406 and/or driving element. In this example, since the resilient barrier is in contact with the driving elements, the resilient barrier does wholly seal the interior of the shaft from fluid contacting the resilient barrier from the surgical site. Hence, the resilient barrier does block the passage of insufflation gas. In a further alternative, one or more of the driving elements contact the resilient barrier 406 and one or more of the other driving elements do not contact the resilient barrier 406.

Figure 7:
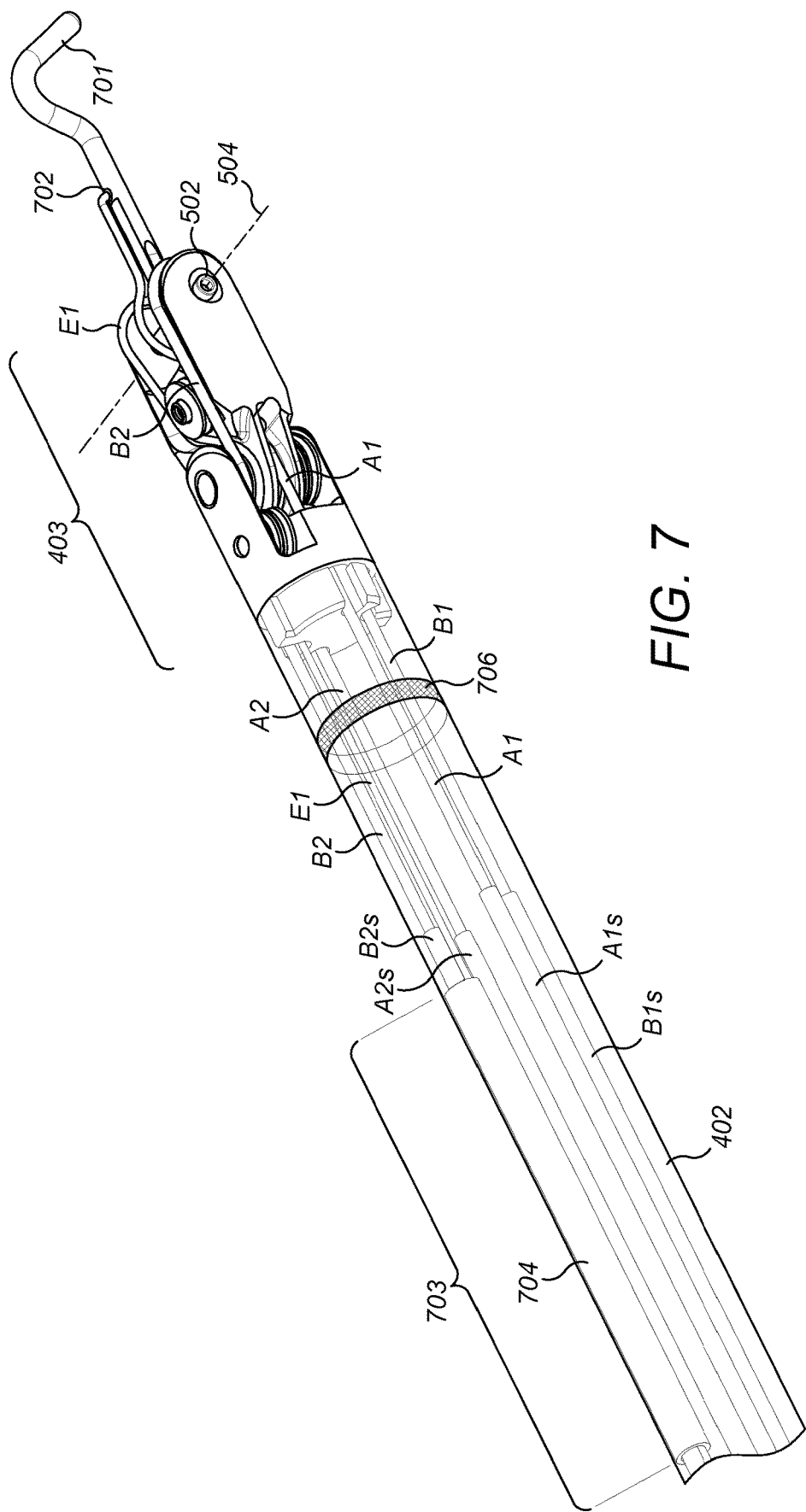
FIG. 7 illustrates the distal end of an electrosurgical instrument.

The figures so far have depicted a surgical instrument having a pair of jaws as the end effector. However, the surgical instrument may have any type of end effector. For example, the instrument may be an electrosurgical instrument having electrosurgical end effectors. For example, FIG. 7 illustrates an electrocautery instrument having an electrocautery end effector for cauterising tissue at the surgical site. The electrocautery end effector 701 illustrated is a monopolar hook. It will be understood that this is for illustrative purposes only. The electrocautery end effector may take any suitable form and shape. For example, the electrocautery end effector may be a bipolar device having two electrocautery end effector elements.

Referring to FIG. 3, for the case that the instrument is an electrocautery instrument, the command interface 312 also comprises one or more inputs whereby the user can request activation and/or deactivation of the electrocautery instrument. The software stored in memory 311 may be configured to respond to these inputs by causing power to the electrocautery instrument to be activated and/or deactivated in compliance with a pre-determined control strategy. The control strategy may include safety features which only cause power to be applied to the electrocautery instrument if certain conditions are met. Alternatively, the input from the user requesting activation/deactivation of power to the electrocautery instrument may bypass the control unit 309 and directly cause power to be applied to/withdrawn from the electrocautery instrument. Alternatively, the input from the user requesting activation/deactivation of power to the electrocautery instrument may pass to a separate control unit from control unit 309. That separate control unit comprises a processor and memory. The memory stores in a non-transient way software that is executable by the processor to apply and withdraw power to the electrocautery instrument in compliance with a pre-determined control strategy. The control strategy may include safety features which only cause power to be applied to the electrocautery instrument if certain conditions are met. Thus, in summary, a surgeon at the command interface 312 can control the electrocautery instrument to move and can also control power to the electrocautery instrument to be activated/deactivated in such a way as to perform a desired surgical procedure.

The articulation 403 and driving elements A1, A2, B1, B2 of the electrocautery instrument of FIG. 7 are as described with respect to FIGS. 4 and 5. The shaft 402 of FIG. 7 houses an additional element E1 compared to the shaft of FIGS. 4 and 5. The additional element is an elongate element which extends from the proximal end of the shaft, through the shaft and the interior of the articulation to the end effector. The additional element can be flexed laterally to its main extent at least in those regions where it engages the internal components of the instrument. In other words, the additional element can be flexed transverse to its longitudinal axis in those regions. This flexibility enables the additional element to wrap around the internal structure of the instrument, such as the joints and pulleys. The additional element may be wholly flexible transverse to its longitudinal axes. Suitably, the additional element is not flexible along its main extent.

Thus, the additional element may resist compression and tension forces applied along its length. In other words, the additional element may resist compression and tension forces acting in the direction of its longitudinal axis. The additional element may have a high modulus. The additional element may remain taut in operation. The additional element may be a cable.

In the example of FIG. 7, the additional element is an electrosurgical element which provides power to the end effector. Specifically, the additional element is an electrocautery element which provides power to the electrocautery end effector. The electrocautery element passes through the interior of the instrument shaft and the interior of the articulation to its connection point 702 with the electrocautery end effector. The electrocautery element may be a power cable. In this case, the electrocautery element is electrically connected to the electrocautery end effector at connection point 702.

The electrocautery element is long enough to fully accommodate movement of the joints of the articulation. This length could interfere with movement of the articulation as a result of the electrocautery element becoming slack and catching on other components internal to the articulation. In order to address this, the electrocautery element E1 may be constrained to wrap around the second axis 504 at least one full revolution in a straight configuration of the electrocautery instrument in which the electrocautery end effector is aligned with the shaft. As the electrocautery end effector 701 is articulated about the second joint 502 in a first rotational direction, the electrocautery element E1 winds about the second axis 504. The electrocautery element E1 thereby accommodates the rotation without becoming slack. As the electrocautery end effector 401 is articulated about the second joint 502 in a second rotational direction which opposes the first rotational direction, the electrocautery element E1 unwinds about the second axis 504. The electrocautery element E1 thereby accommodates the rotation without becoming so taut as to restrict the rotation of the electrocautery end effector in the second rotational direction.

Alternatively, or additionally, the electrocautery element may be constrained by the resilient barrier 406. A plan view of resilient barrier 706 is shown in FIG. 6b. Resilient barrier 706 is as described with reference to FIGS. 4, 5 and 6a except that the additional element E1 additionally extends through the resilient barrier 706. Additional element E1 passes through a hole 605 in the resilient barrier. In contrast to the driving elements, additional element E1 does contact the resilient barrier. Thus, the diameter of hole 605 is the same as or slightly smaller than the diameter of the additional element E1. The resilient barrier deforms around the additional element E1. The resilient barrier is in resilient contact with the additional element E1 so as to provide a resilient force opposing movement of the additional element E1. The resilient barrier provides a spring like force to the additional element E1, acting to return the additional element E1 to its original position when the additional element E1 is pulled either towards the proximal end of the shaft or towards the end effector. The resilient contact between the resilient barrier 706 and the additional element E1 thus helps to stop slack of the additional element E1 bunching up in the articulation.

The additional element E1 may be secured to a driving element in the shaft 402. For example, the additional element E1 may be bonded to a driving element for a portion of the shaft. This prevents the additional element E1 from catching on and interfering with the driving elements in the shaft. The additional element E1 may be crimped to a driving element. The additional element E1 is not secured to a driving element in any region in which the additional element is constrained to interact with structure of the instrument, for example pulleys, joints, or the resilient barrier. If the additional element E1 is secured to a driving element in a portion of the shaft, then the resilient barrier is located between that portion of the shaft and the articulation. FIG. 7 illustrates an example in which additional element E1 is secured to driving element B2 in portion 703 of shaft 402. Sheath 704 encompasses additional element E1 and driving element B2, thereby securing them to each other. Resilient barrier 706 is located in the shaft between portion 703 and articulation 403.

The driving elements may be composed of different portions. For example, the portions of each driving element which engage the instrument interface and the articulation may be flexible. Between these flexible portions, the driving element may be a spoke. These spokes are denoted $A1s$, $A2s$, $B1s$, $B2s$ in FIG. 7. The spokes are wholly enclosed in the shaft 402. The spokes are stiffer than the flexible portions of the driving elements. The spokes may be rigid. As shown in FIG. 7, the additional element E1 may be bonded to the spoke $B2s$ of one of the driving elements B2. The additional element E1 may be bonded to the spoke for most of the length of the shaft. In FIG. 7, the driving elements are flexible (for example cables) at the location in which they pass through holes in the resilient barrier. Alternatively, the driving elements may be spokes at the location in which they pass through holes in the resilient barrier. One or more of the driving elements may be spokes whilst one or more other of the driving elements may be flexible at the location in which they pass through holes in the resilient barrier.

The resilient barrier is fabricated from a material which is deformable about the additional element. The resilient barrier squeezes around the additional element so as to provide a resistive contact with the additional element. Suitably, the resilient barrier is impermeable to insufflation gases used in surgery, for example $CO_2$. The resilient barrier may also be impermeable to water-based liquids, such as those found in the body. The resilient barrier may be fabricated from silicone. Alternatively, the resilient barrier may be fabricated from one of neoprene, natural rubber, nitrile rubber, butyl rubber, synthetic rubber, PVC and a thermoplastic elastomer.

In the instrument described with respect to FIG. 7, the resilient barrier has the dual effects of (i) reducing the leakage rate of insufflation gas from the surgical site, and (ii) tensioning the electrosurgical element to avoid slack getting caught in the articulation.

In all the instruments described, the resilient barrier does not substantially constrain the motion of the driving elements. This is because movement of the end effector is very finely tuned by the instrument interface elements driving the driving elements. If the resilient barrier were to constrain the driving elements in the same way as it constrains the additional element, an unknown and inconsistent frictional force would be applied to the driving elements which would affect the relationship between the movement of the instrument interface elements and the movement of the distal driving elements at the joints they are driving in an unpredictable way.

In FIG. 7, the additional element E1 that is constrained by the resilient barrier is an electrosurgical element. That electrosurgical element may be used to deliver power to the electrosurgical end effector. The use of an additional element E1 as described above is not limited to electrosurgical instruments. The additional element E1 and resilient barrier as described above may be used with other energy delivery instruments in which energy is supplied to the end effector via an element (i.e. additional element E1) in the shaft. More generally, the additional element E1 and resilient barrier as described above may be used with any instrument in which an element (i.e. additional element E1) is to pass through the articulation 403 to the end effector, where that element is not maintained taught. Examples of such elements are electrical leads, fibre optic conduits, tubes for administering or removing material, and conduits for other energy forms (such as vibration).

FIG. 7 illustrates a monopolar hook end effector which is powered by a single additional element E1. However, there may be one or more further additional elements in the shaft. For example, for the case that the electrocautery end effector is a bipolar device having two electrocautery end effector elements, those two end effector elements may be powered by separate additional elements. In the case that there are further additional elements in the shaft, each additional element is treated the same as the additional element described herein. In other words, each additional element passes through the resilient barrier in resilient contact with the resilient barrier as described herein.

FIGS. 8(a) and 8(b) show an alternative embodiment in which the resilient barrier 801 comprises a cantilever part, shown generally at 802. The cantilever part 802 is an additional part of the resilient barrier from the part of the barrier that extends over a cross-sectional area of the shaft. The cantilever part 802 protrudes from the part of the resilient barrier that extends over the cross-sectional area of the shaft. The cantilever part 802 may be integrally formed with the part of the resilient barrier that extends over the cross-sectional area of the shaft.

The part of the resilient barrier that extends over the cross section of the shaft has a hole 803 in it through which the additional element E1 and at least one of the driving elements pass. Only the driving element A1 is shown in FIGS. 8(a) and 8(b). The other driving elements A2, B1 and B2 may also pass through hole 803, or they may pass through additional holes in the resilient barrier 801. There may therefore be multiple such holes in the resilient barrier.

The hole 803 may be frustoconical in shape. The through hole 803 may be formed by forming recesses or blind holes in the material comprising the resilient barrier from each side of the resilient barrier. The blind holes may each be frustoconical in shape. During assembly, the piece of material joining the recesses or blind holes can be removed using a punch to create the through hole 803.

The hole 803, or the recesses or blind holes from which the through hole is formed, may be moulded into the resilient material from which the resilient barrier is formed.

In this embodiment, the cantilever part 802 of the resilient barrier provides the resilient force on the additional element. The additional element E1 passes through holes 804 and 805 in the cantilever part 802. The holes 804, 805 extend through the cantilever part approximately transverse to the longitudinal axis of the shaft when the resilient barrier is installed in the shaft. As shown in FIGS. 8(a) and (b), the additional element E1 is looped through the holes 804 and 805 in the cantilever part 802 and then continues along the axis of the shaft towards the proximal and distal ends of the shaft. The additional element is in contact with the resilient barrier as it passes through holes 804 and 805.

The cantilever part 802 is capable of bending relative to the axis of the shaft to provide a further resilient force on the additional element. As the surgical instrument (not shown in FIGS. 8(a) and 8(b)) articulates, the cantilever 802 is pulled sideways as indicated by arrow 806 to provide a force on the additional element E1. The cantilever may be straight, as shown in FIGS. 8(a) and 8(b), or it may be curved.

The hole 803 may have a larger diameter than the holes 804 and 805. The hole 803 may be D-shaped in cross section. The holes 804 and 805 through the cantilever part 802 may be cylindrical (i.e. they may have circular cross sections).

In this embodiment, the resilient force opposing movement of the additional element is therefore provided by an additional part of the resilient barrier to the part that extends over a cross-sectional area of the shaft. The additional element passes through at least one hole in the additional part in resilient contact with the resilient barrier so as to provide a resilient force opposing movement of the additional element. The additional element and at least one of the driving elements pass through a hole in the part of the resilient barrier which extends over a cross-sectional area of the shaft without contacting the resilient barrier. The additional part of the resilient barrier may be a cantilever which is capable of bending relative to the longitudinal axis of the shaft to provide a further resilient force on the additional element opposing movement of the additional element.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument comprising:
    a shaft;
    an end effector;
    an articulation connecting the end effector to a distal end of the shaft, the articulation comprising joints permitting the end effector to adopt a range of orientations relative to a longitudinal axis of the shaft;
    pairs of driving elements configured to drive the joints, the driving elements extending through the shaft to the joints;
    an additional element extending through the shaft to the end effector via the articulation; and
    a resilient barrier inside the shaft extending over a cross-sectional area of the shaft, the pairs of driving elements and the additional element passing through the resilient barrier, the resilient barrier in resilient contact with the additional element so as to provide a resilient force opposing movement of the additional element;
    wherein the additional element is secured to one of the driving elements in a first portion of the shaft, the resilient barrier being located between the first portion of the shaft and the articulation.

2. A robotic surgical instrument as claimed in claim 1, wherein the resilient barrier is configured to inhibit passage of fluid through the shaft from one side of the resilient barrier to the other.

3. A robotic surgical instrument as claimed in claim 2, wherein the resilient barrier is configured to inhibit passage of insufflation gas through the shaft from one side of the resilient barrier to the other.

4. A robotic surgical instrument as claimed in claim 1, wherein the cross-sectional area is transverse to the longitudinal axis of the shaft.

5. A robotic surgical instrument as claimed in claim 1, wherein an outer edge of the resilient barrier is in sealed contact with the interior wall of the shaft around the outer edge of the cross-sectional area.

6. A robotic surgical instrument as claimed in claim 1, wherein the additional element passes through an additional hole in the resilient barrier, the diameter of the additional hole in the resilient barrier being less than or the same as the diameter of the additional element where it passes through the additional hole in the resilient barrier.

7. A robotic surgical instrument as claimed in claim 1, wherein the robotic surgical instrument is an electrosurgical instrument having an electrosurgical end effector, the additional element being an electrosurgical element configured to provide power to the electrosurgical end effector.

8. A robotic surgical instrument as claimed in claim 1, wherein the resilient barrier is located at the distal end of the shaft.

9. A robotic surgical instrument as claimed in claim 1, wherein the additional element is secured to a spoke of the driving element in the first portion of the shaft.

10. A robotic surgical instrument as claimed in claim 1, further comprising an instrument interface connected to a proximal end of the shaft, the instrument interface having an open structure through which fluid can move.

11. A robotic surgical instrument as claimed in claim 1, wherein the additional element is configured to wrap around at least one revolution of a joint of the articulation when the instrument is in a straight configuration in which the end effector is aligned with the shaft.

12. A robotic surgical instrument as claimed in claim 1, wherein the resilient barrier is fabricated from silicone.

13. A robotic surgical instrument as claimed in claim 1, wherein the portion of the additional element which passes through the resilient barrier is flexible.

14. A robotic surgical instrument as claimed in claim 1, wherein the additional element is a cable.

15. A robotic surgical instrument as claimed in claim 1, further comprising a further additional element extending through the resilient barrier in the shaft to the end effector via the articulation, the further additional element in resilient contact with the resilient barrier.

16. A robotic surgical instrument as claimed in claim 15, wherein the end effector comprises first and second end effector elements, the additional element being connected to the first end effector element, the further additional element being connected to the second end effector element.

17. A robotic surgical instrument as claimed in claim 16, wherein the additional element is configured to provide power to the first end effector element, and the further additional element is configured to provide power to the second end effector element.

18. A robotic surgical instrument as claimed in claim 1, wherein each driving element of the pairs of driving elements passes through a hole in the resilient barrier without contacting the resilient barrier.

\* \* \* \* \*